(12) United States Patent
Noerenberg et al.

(10) Patent No.: US 7,494,966 B2
(45) Date of Patent: Feb. 24, 2009

(54) ALKOXYLATES THAT ARE STABLE IN ALKALIS

(75) Inventors: Ralf Noerenberg, Ingelheim (DE); Ulrich Annen, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 229 days.

(21) Appl. No.: 10/570,307

(22) PCT Filed: Sep. 6, 2004

(86) PCT No.: PCT/EP2004/009904

§ 371 (c)(1), (2), (4) Date: Mar. 2, 2006

(87) PCT Pub. No.: WO2005/026094

PCT Pub. Date: Mar. 24, 2005

(65) Prior Publication Data

US 2007/0037725 A1    Feb. 15, 2007

(30) Foreign Application Priority Data

Sep. 10, 2003 (DE) ............... 103 41 724

(51) Int. Cl.
  *C11D 1/72* (2006.01)
  *C11D 13/10* (2006.01)
(52) U.S. Cl. .............. 510/421; 510/245; 510/360; 510/365; 510/413; 510/475; 510/505; 510/506; 510/524; 134/38; 134/39; 134/40; 134/41; 134/42
(58) Field of Classification Search .......... 510/245, 510/360, 365, 413, 421, 475, 505, 506, 524; 134/38, 39, 40, 41, 42
See application file for complete search history.

(56) References Cited

U.S. PATENT DOCUMENTS

| | | | |
|---|---|---|---|
| 3,407,142 A | 10/1968 | McCord et al. | |
| 4,753,885 A | 6/1988 | Dietsche et al. | |
| 4,973,423 A | 11/1990 | Geke et al. | |
| 5,071,454 A | 12/1991 | Streitberger et al. | |
| 5,099,255 A * | 3/1992 | Koike et al. | 347/100 |
| 5,677,273 A | 10/1997 | Schmid et al. | |
| 6,133,218 A * | 10/2000 | Kerobo et al. | 510/365 |

FOREIGN PATENT DOCUMENTS

| | | |
|---|---|---|
| DE | 36 26 567 | 2/1987 |
| EP | 1 050 524 | 11/2000 |
| WO | 03/060049 | 7/2003 |

OTHER PUBLICATIONS

Hobin, T.P. "Model Polyethers I-Synthesis by the Williamson Reaction", Polymer, vol. 6, pp. 403-409, 1965, no month given.
Matasuura, Hiroatsu et al: "Raman Spectroscopic studies of Molecular Conformation of alpha-alkyl-omega-alkoxyoligo-(oxyethylene)s", Journal of Molecular Structure, vol. 189, pp. 249-256, 1988, no month given.
Chen, Yiyan et al: "Synthesis and Properties of ABA Amphiphiles", Journal of Org. Chem., vol. 64, No. 18, pp. 6870-6873, 1999, Aug. 18, 1999.

* cited by examiner

*Primary Examiner*—Brian P Mruk
(74) *Attorney, Agent, or Firm*—Oblon, Spivak, McClelland, Maier & Neustadt, P.C.

(57) ABSTRACT

A description is given of an alkanol-free alkoxylate of the general formula (I)

$$C_nH_{2n+1}O(A)_x(B)_yR \qquad (I)$$

where
R is $C_{1-6}$ alkyl or benzyl
A is ethyleneoxy
B is $C_{3-6}$ alkyleneoxy or mixtures thereof,
it being possible for groups A and B to be in random distribution, in alternation or in the form of two or more blocks in any order,
n is an integer in the range from 4 to 8
x is a number in the range from 0 to 25
y is a number in the range from 0 to 10
and x+y is at least 3.

20 Claims, No Drawings

ALKOXYLATES THAT ARE STABLE IN ALKALIS

The invention relates to alkali-stable alkoxylates, to processes for preparing them, to their use and to formulations comprising the alkoxylates.

The rapid wetting of surfaces plays a key part in many areas of everyday life and in numerous industrial operations, such as in the cleaning or coating of substrates, for example. In many formulations, therefore, varying amounts of alcohols such as ethanol or isopropanol are used in order, for example, to lower the interfacial or surface tension and so to improve the wetting capacity of the formulations. In this context it is usual to admix aqueous formulations with often relatively large amounts of these alcohols. The physiological effect of the alcohols, however, is objectionable, and the exposure suffered by the user of such formulations is high, owing to the high vapor pressure of the alcohols. Consequently, nowadays, in formulations for example that are handled directly by the user, there should be only small amounts of alcohols or none at all. For formulations providing very rapid wetting, such as fountain solutions in the printing industry or additives for coating formulations, spray coatings for example, however, these alcohols continue to constitute a necessary ingredient.

For some years now the very effectively wetting action of very hydrophobic, compact alcohols, which can be prepared from acetylene and aldehydes, has been known. The alcohols in question are, in particular, dihydroxyalkynes. These products, however, are not compatible with every cleaning product formulation and can often be used only with the aid of solubilizers such as cumenesulfonate, ethylene glycol, etc. It is often necessary to use a fairly large amount of the solubilizer in comparison to the wetting assistant, giving rise to high sequential costs as a result of the use of the dihydroxyalkynes. Moreover, the action of the wetting assistant is impaired when it is blended with relatively large amounts of solubilizers.

One common way of increasing the wetting rate of aqueous formulations is to use surfactants, which accumulate at interfaces, where they lower the surface tension. While adding alcohols such as ethanol or isopropanol to aqueous formulations gives the resulting water/solvent mixture a surface tension lower than water and hence an improved wetting behavior, wetting or surface coverage when using surfactant systems is time-dependent.

The surfactant molecules must first diffuse to the surface and build up an interface film thereon, thereby lowering the interfacial tension or surface tension on contact with water and air. In the case of very rapid operations such as spraying or wetting operations, for instance, such as those of coating materials in curtain coating operations, the time within which the interfacial or surface tension is lowered by the surfactant system to the equilibrium value is critical. The dynamics of the surfactant system are of great importance to the wetting rate.

Presently alcohol ethoxylates of lower alcohols are used as suitable wetting agents. As an inevitable result of their preparation, however, such products frequently contain amounts of alcohol, which again contributes critically to rapid wetting and in the case of very short wetting times may be the only wetting component.

The use of alkyl glycol alkoxylates or alkyl diglycol alkoxylates, which are obtainable by alkoxylating $C_{4-8}$ alkyl glycols or diglycols with $C_{2-5}$ alkoxides to an average degree of alkoxylation from 1 to 8, based on $C_{4-8}$ alkyl glycols or diglycols, in aqueous formulations is known from WO 03/60049.

In alkaline formulations, however, polyalkoxylates frequently lack adequate stability. The chemical instability of polyalkoxylates derives from chain degradation as a consequence of deprotonation of the terminal alcohol function.

It is an object of the present invention to provide alkanol-free alkoxylates which can be used for reducing the surface tension and accelerating the establishment of the surface tension in aqueous surfactant formulations or aqueous dispersions, for example, and which exhibit improved stability with respect to alkaline media. The improvement in the stability with respect to alkalis should preferably not be accompanied by any substantial deterioration in the wetting behavior for different substrate surfaces.

This object is achieved in accordance with the invention by means of an alkanol-free alkoxylate of the general formula (I)

$$C_nH_{2n+1}O(A)_x(B)_yR \qquad (I)$$

where
R is $C_{1-6}$ alkyl or benzyl
A is ethyleneoxy
B is $C_{3-6}$ alkyleneoxy or mixtures thereof,
it being possible for groups A and B to be in random distribution, in alternation or in the form of two or more blocks in any order,
n is an integer in the range from 4 to 8
x is a number in the range from 0 to 25
y is a number in the range from 0 to 10
and x+y is at least 3.

R is a $C_{1-6}$ alkyl radical, which may be linear or branched, or a benzyl radical. Preferably R is a $C_{1-3}$ alkyl radical, in particular a linear $C_{1-3}$ alkyl radical, especially methyl, ethyl or propyl, particularly methyl.

B is $C_{3-6}$ alkyleneoxy or mixtures thereof, preferably propyleneoxy or butyleneoxy, particularly propyleneoxy.

x is a number in the range from 0 to 25, preferably 3 to 25, more preferably 5 to 15, in particular 5 to 12.

y is a number in the range from 0 to 10, preferably 0, 1 or 2.

The radical $C_nH_{2n+1}$ may comprise linear or singly or multiply branched alkyl radicals, with the presence of mixtures of linear or branched alkyl radicals also being possible. With particular preference there is a linear and hence terminal alkyl radical.

The compounds of the invention of the general formula (I) are obtained, for example, by alkoxylating alcohols of the general formula $C_nH_{2n+1}OH$ with alkylene oxides corresponding to the units A and B. The alkoxylation is followed by an etherification, with dimethyl sulfate, for example.

The values of x and y represent averages, since the alkoxylation of alkanols generally results in a distribution of the degree of alkoxylation. Consequently x and y may differ from integral values. The distribution of the degree of alkoxylation can be adjusted to a certain extent by using different alkoxylation catalysts. Where, in addition to ethylene oxide, one or more longer-chain alkylene oxides are used for the alkoxylation, the different alkylene oxide radicals may be in random distribution, in alternation or in the form of two or more blocks in any order. Particular preference is given to alkoxylating only with ethylene oxide, so that there is a simple (poly)ethylene oxide radical. The average of the homologous distribution is represented by the stated numbers x and y.

The alkoxylation can be carried out, for example, using alkaline catalysts such as alkali metal hydroxides or alkali metal alcoholates. Use of these catalysts results in specific properties, in particular the distribution of the degree of alkoxylation.

The alkoxylation can also be carried out using Lewis acid catalysis with the resultant specific properties, in particular in the presence of $BF_3 \times H_3PO_4$, $BF_3$ dietherate, $BF_3$, $SbCl_5$, $SnCl_4 \times 2H_2O$, hydrotalcite. Also suitable as catalyst are double metal cyanide (DMC) compounds.

The excess alcohol can be distilled off or the alkoxylate can be recovered by a two-stage operation. Also possible is the preparation of mixed alkoxylates from EO and PO, for example, in which the alkanol radical may be followed first by a propylene oxide block and then by an ethylene oxide block, or first an ethylene oxide block and then a propylene oxide block. Random/statistical distributions are possible as well. Preferred reaction conditions are indicated below.

The alkoxylation is preferably catalyzed by strong bases, which are advantageously added in the form of an alkali metal hydroxide or alkaline earth metal hydroxide, generally in an amount of from 0.1 to 1% by weight, based on the amount of the alkanol R2-OH (cf. G. Gee et al., J. Chem. Soc. (1961), p. 1345; B. Wojtech, Makromol. Chem. 66, (1966), p. 180).

Acidic catalysis of the addition reaction is also possible. Suitable acids, as well as Brønsted acids, include Lewis acids, such as $AlCl_3$ or $BF_3$. (cf. P. H. Plesch, The Chemistry of Cationic Polymerization, Pergamon Press, New York (1963)).

As a DMC compound it is possible in principle to use all of the suitable compounds that are known to the skilled worker.

DMC compounds suitable as catalysts are described, for example, in WO 99/16775 and DE-A-10117273. Catalysts suitable for the alkoxylation include in particular double metal cyanide compound of the general formula:

in which
  $M^1$ is at least one metal ion selected from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$ and $Ru^{3+}$,
  $M^2$ is at least one metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$ and $Ir^{3+}$,
  A and X independently of one another are each an anion selected from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate or hydrogencarbonate,
  L is a water-miscible ligand selected from the group consisting of alcohols, aldehydes, ketones, ethers, polyethers, esters, polyesters, polycarbonate, ureas, amides, primary, secondary and tertiary amines, ligands containing pyridine nitrogen, nitriles, sulfides, phosphides, phosphites, phosphanes, phosphonates and phosphates,
  k is a fractional or integral number greater than or equal to zero, and
  P is an organic additive,
  a, b, c, d, g and n are selected such that the electroneutrality of the compound (I) is ensured, it being possible for c to be 0,
  e is the number of ligand molecules and is a fractional or integral number greater than 0 or 0,
  f, h and m independently of one another are each a fractional or integral number greater than 0 or 0.

Organic additives P include the following: polyethers, polyesters, polycarbonates, polyalkylene glycol sorbitan esters, polyalkylene glycol glycidyl ethers, polyacrylamide, poly(acrylamide-co-acrylic acid), polyacrylic acid, poly (acrylamide-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkylenimines, maleic acid copolymers and maleic anhydride copolymers, hydroxyethylcellulose, polyacetates, ionic surface-active and interface-active compounds, gallic acid or the salts, esters or amides thereof, carboxylic esters of polyhydric alcohols, and glycosides.

These catalysts may be crystalline or amorphous. Where k is zero, crystalline double metal cyanide compounds are preferred. Where k is greater than zero, not only crystalline and semicrystalline but also substantially amorphous catalysts are preferred.

There are different preferred embodiments of the modified catalysts. One preferred embodiment comprises catalysts of the formula in which k is greater than zero. In that case the preferred catalyst comprises at least one double metal cyanide compound, at least one organic ligand and at least one organic additive P.

In another preferred embodiment k is zero, optionally e is zero as well and X is exclusively a carboxylate, preferably formate, acetate and propionate. Catalysts of this kind are described in WO 99/16775. In this embodiment crystalline double metal cyanide catalysts are preferred. Preference is also given to double metal cyanide catalysts, as described in WO 00/74845, which are crystalline and platelet-shaped.

The modified catalysts are prepared by combining a metal salt solution with a cyanometallate solution, which optionally may contain not only an organic ligand L but also an organic additive P. Subsequently the organic ligand and, optionally, the organic additive are added. In one preferred embodiment of the catalyst preparation first of all an inactive double metal cyanide phase is prepared and subsequently this phase is converted by recrystallization into an active double metal cyanide phase, as described in PCT/EP01/01893.

In another preferred embodiment of the catalysts f, e and k are other than zero. These are double metal cyanide catalysts containing a water-miscible organic ligand (generally in amounts of from 0.5 to 30% by weight) and an organic additive (generally in amounts of from 5 to 80% by weight) as described in WO 98/06312. The catalysts can be prepared either with vigorous stirring (24,000 rpm with Turrax) or with stirring, as described in U.S. Pat. No. 5,158,922.

Particularly suitable catalysts for the alkoxylation are double metal cyanide compounds containing zinc, cobalt or iron or two of these. A particularly suitable example is Prussian Blue.

It is preferred to use crystalline DMC compounds. In one preferred embodiment a crystalline DMC compound of the Zn—Co type is used as catalyst, containing zinc acetate as a further metal salt component. Such compounds crystallize in monoclinic structure and have a platelet-shaped habit. Compounds of this kind are described, for example, in WO 00/74845 or PCT/EP01/01893.

DMC compounds suitable as catalysts can be prepared in principle in any way known to the skilled worker. For example, the DMC compounds can be prepared by direct precipitation, the "incipient wetness" method, by preparing a precursor phase and subsequent recrystallization.

The DMC compounds can be used as a powder, paste or suspension or can be shaped to a molding, introduced into moldings, foams or the like or applied to moldings, foams or the like.

The catalyst concentration used for the alkoxylation, based on the final quantitative parameters, is typically less than 2000 ppm, preferably less than 1000 ppm, in particular less than 500 ppm, more preferably less than 100 ppm, for example less than 50 ppm.

The addition reaction is performed in a closed vessel at temperatures of about 90 to about 240° C., preferably from 120 to 180° C. The alkylene oxide or the mixture of different alkylene oxides is supplied to the mixture of inventive alkanol mixture and alkali under the alkylene oxide mixture vapor pressure which prevails at the chosen reaction temperature. The alkylene oxide can be diluted if desired with up to about 30 to 60% with an inert gas. This provides additional security against explosive polyaddition of the alkylene oxide.

If an alkylene oxide mixture is used then polyether chains are formed in which the different alkylene oxide building blocks are distributed virtually at random. Variations in the distribution of the building blocks along a polyether chain arise as a result of different reaction rates of the components and may also be achieved arbitrarily by continuously supplying an alkylene oxide mixture whose composition is under program control. Where the different alkylene oxides are reacted in succession the products are polyether chains with a blockwise distribution of the alkylene oxide building blocks.

The length of the polyether chains within the reaction product fluctuates statistically around an average value which corresponds essentially to the stoichiometric value resulting from the amount added.

To prepare the compounds of the general formula (I) it is also possible to use alkyl glycol alkoxylates or alkyl diglycol alkoxylates which are obtainable by alkoxylating $C_{4-8}$ alkyl glycols or diglycols with $C_{2-5}$ alkoxides, preferably up to an average degree of alkoxylation of from 1 to 24 or 23, based on the $C_{4-8}$ alkyl glycols or diglycols. These products are then etherified, with H in the terminal hydroxyl group being replaced by R.

The remarks below refer to alkyl diglycols and also to alkyl glycols and their alkoxylates.

The parent alkyl glycols can be linear or branched alkyl glycols. Attachment of the $C_{4-8}$ alkyl radical to the glycol may take place terminally or at any other position along the alkyl chain. The glycols are preferably linear alkyl glycols, especially linear, terminal alkyl glycols. The alkyl radicals of the alkyl glycols preferably have 5 to 8 carbon atoms. The degree of alkoxylation is preferably on average from 2 to 24 or from 1 to 23, more preferably from 4 to 14 or from 3 to 13, based on the glycols or diglycols respectively. For the alkoxylation it is possible with preference to use $C_{2-4}$ alkoxides. Preference is given to using ethylene oxide, propylene oxide, butylene oxide or mixtures thereof. With particular preference ethylene oxide is used. The preferred ranges relate to the alkyl glycol alkoxylates and alkyl diglycol alkoxylates per se.

Preparation takes place here starting from alcohol-free, preferably pure alkyl glycols and alkyl diglycols, and not, as described above, from alkanols, by alkoxylation. Therefore the product mixtures do not contain any remaining alkanols, but only, at most, alkyl glycols. The result is a distribution of the degree of alkoxylation that is specific for alkyl glycols. As a result of the preparation process the alkyl glycol alkoxylates are free from alcohols.

Alkoxylates are oligomeric or polymeric reaction products with alkoxides. Owing to the kinetics of polymerizations, which are known to the skilled worker, there is automatically a statistical distribution of homologs, the average value of which is normally reported. The frequency distribution of the homologs includes the starting material, particularly for low degrees of alkoxylation. Although it is possible to influence the distribution to a certain extent through the choice of catalyst, there is nothing different in principle about the distribution curve. Pure alkyl oligoglycols can be prepared only by means of distillative or chromatographic workup and are therefore expensive. Moreover it has been found that the distribution of the homologs has an advantageous influence on the aggregation behavior.

The etherified alkoxylates described in this embodiment possess the homolog distribution which is important for the aggregation behavior and the other properties according to the invention, without containing alcohol.

The products obtained by the other processes are freed from remaining alkanols.

The expression "alkanol-free" refers to alkoxylates which have no measurable quantities of alkanols according to gas chromatography (GC), particularly of $C_nH_{2n+1}OH$.

The distribution of the degrees of alkoxylation can be determined by chromatographic methods.

For a comparison between alkanol alkoxylates and alkyl glycol alkoxylates reference may be made to WO 03/60049.

Since the product mixture contains no alcohols it is largely odorless. The compounds of the formula (I) can be used—particularly in the stated applications—in combination with surfactants. Surfactants which can be used in accordance with the invention are any surfactants which in solution in an amount of 5 g/l of water have a surface tension of less than 45 mN/m at 20° C. The surfactants can, generally speaking, be alkoxylated alcohols, amides, acids, betaines, amine oxides or amines, but also dihydroxyalkynes and derivatives and mixtures thereof. The rate at which the end level of the surface tension is established may depend on the molecular architecture, such as the chain length and degree of branching of the alcohol, the length and solvation of the alkoxylate, the surfactant concentration and the aggregation of surfactant. In general, smaller aggregates diffuse more rapidly than do large aggregates.

The surfactants are preferably nonionic surfactants and are selected from $C_{2-5}$, preferably $C_{2-4}$ alkoxylates of $C_{9-20}$, preferably $C_{9-15}$, in particular $C_{9-13}$ alkanols, having on average a degree of alkoxylation of from 3 to 40, preferably 4-15, in particular from 5 to 12, and mixtures thereof. The alkanols in question may be linear or branched. In the case of a branched alcohol the degree of branching is preferably in the range from 1.1 to 1.5. The alkoxylation can take place with any desired $C_{2-4}$ alkoxides and mixtures thereof.

Alkoxylation can be performed, for example, with ethylene oxide, propylene oxide or butylene oxide. Particular preference is given to using ethylene oxide, propylene oxide or mixtures thereof. Ethylene oxide is particularly preferred. Nonionic surfactants of this kind are known and are described, for example, in EP-A-0 616 026 and EP-A-0 616 028. Those publications also mention shorter-chain alkyl alkoxylates.

The nonionic surfactants used can also be replaced by dihydroxyalkynes or derivatives thereof. The surfactants in question may also be low-foam surfactants or foam-suppressing surfactants; cf. also EP-A-0 681 865. Low-foam and foam-suppressing surfactants are known to the skilled worker.

The invention also provides for the use of the alkanol-free alkoxylates in alkaline formulations comprising solvent or diluent. In that application they are used in particular to improve the wetting effect of the formulations. The formulations generally comprise water or organic solvents or diluents. The pH of these formulations is preferably more than 10, more preferably more than 12.

Suitable formulations comprise, for example, the alkoxylates and also at least one surfactant and water.

The invention further provides a cleaning, degreasing, metal-cleaning or wetting composition or crop protection formulation comprising an alkoxylate of the invention.

The invention additionally provides varnishes, paint formulations, formulations for spray applications, mineral processing, the printing industry, the paper and wood industry or for coatings, coating compositions, adhesive compositions, leather treatment compositions, metal treatment compositions, metalworking compositions, foaming assistants or textile treatment compositions comprising an alkoxylate of the invention.

The coating composition can be, for example, a formulation for spray applications.

In the case of a coating formulation the formulation may in particular be a coating formulation applied by blade coating, spray coating or curtain coating.

The object is further achieved in accordance with the invention through the use of the alkoxylates for reducing surface tension, in particular in short times of usually less than 1 second, and accelerating the establishment of surface tension in aqueous surfactant formulations or aqueous dispersions.

The object is further achieved through the use of the alkoxylates for increasing the wetting rate in aqueous wetting compositions.

The alkoxylates of the invention can be used for formulating compositions in all sectors which employ highly dynamic formulations, particularly under alkaline conditions. Examples thereof are:

general-purpose cleaners, spray cleaners for cleaning in the industrial and institutional sector, including metalworking, print roller and printing plate cleaning compositions in the printing industry, varnishes, paint formulations, coating compositions, for paper for example, such as paper coating colors, wood binders, especially formaldehyde resins, adhesives in the lacquer and film industry, in dispersion form for example, formulations for spray applications, metal treatment and metalworking such as corrosion control formulations, cutting, grinding or drilling assistants, drilling fluids and lubricants, including cooling lubricants, formulations in the textile industry, formulations for the leaching of ores, by the cyanide process, for example, formulations for rendering pigments or particles hydrophilic for the purpose of binding finely divided pigments and starches.

Such formulations normally include further ingredients such as surfactants, complexing agents, polymers and other ingredients.

Generally speaking, the mixtures of the invention can be used in all sectors where the action of surface-active substances is required, especially under alkaline conditions.

Through the use of non-surfactant structures the formulations of the invention are more environmentally compatible and skin-compatible than systems described, for example, in EP-A-0 616 026. Unlike the customary solubilizers such as cumenesulfonate, the interaction is specifically with the surfactants. Thus the alkoxylated alkyl glycols used in accordance with the invention engage actively in covering the interface and accelerate the establishment of the interface equilibrium.

It is neither necessary nor desirable in accordance with the invention for there to be a residual alcohol content in the mixtures or formulations of the invention. In accordance with one embodiment the mixtures, compositions and formulations of the invention are free from alcohols and preferably also from alkyl glycols or diglycols, particularly from $C_{4-8}$ alkyl glycols and $C_{9-13}$ alkanols. In accordance with the invention it has been found that without a residual alcohol content, which is normally present, as an inevitable consequence of the preparation process, in the case of lower alcohol alkoxylates, the use of the alkyl glycol alkoxylates of the invention allows surfactant formulations to be formulated with high interface dynamics.

The wetting effect of the invention can be determined by means of a dynamic measurement of the surface tension, using for example a bubble pressure tensiometer. A corresponding approach is described, for example, in S. S. Dukhen, G. Kretzschmar, R. Miller (Ed.), Dynamics of adsorption at liquid interfaces, Elsevier, 1995. The wetting effect on surfaces can be determined by a dynamic measurement of the interfacial tension. One such method is that of video-assisted, time-resolved contact angle measurement.

The invention also provides for the use of the alkoxylates in the surface finishing. The invention accordingly provides a coating composition which is an aqueous paper coating dispersion comprising water, pigments, binder and from 0.05 to 5% by weight, based on the pigments, of alkoxylates of the invention. The formulations may comprise natural or synthetic binders or mixtures thereof. Further possible ingredients are rheological assistants, dispersants, thickeners, etc.

In the coating compositions the droplet size may then be influenced significantly in a spray coating operation, in conjunction with a low foam deficiency of the spray coating materials or paint formulations.

The pigments used in the coating compositions normally constitute the main component. It is possible to use any pigments which are commonly employed, such as calcium carbonates, kaolin, talc, titanium dioxide, gypsum, chalk, carbon black or synthetic pigments, alone or in a mixture.

The alkoxylate is usually used in amounts of from 0.05 to 5%, based on the formulation, preferably in amounts of from 0.1 to 2%. The alkoxylate can be added not only during the operation of preparing the formulation directly (and/or) but also in a mixture with a constituent of the coating color (e.g., a pigment slurry and/or a binder).

The invention is illustrated below with reference to examples:

EXAMPLE 1

Chemical Stability

An alkyl alkoxylate of the invention (hexanol+9 EO, methylated with dimethyl sulfate) is dissolved in 5% strength NaOH. GPC investigation after different times shows that there is no observable change in the peak structure.

EXAMPLE 2

Surface-active Effect

On a 0.5% strength solution of an alkoxylate of the invention (see above) the surface tension is determined in time-resolved form using a bubble pressure tensiometer (Tz. H. Iliev, C. D. Dushkin, *Colloid Polym. Sci.* 270 (1992) 370). A reduction in the surface tension from 72 mN/m to 32 mN/m is found within the first 20 ms.

What is claimed is:

1. A method of increasing the wetting rate of an alkaline formulation comprising water, an organic solvent or a diluent, wherein said method comprises:

adding to the alkaline formulation at least one alkanol-free alkoxylate of the following general formula (I):

$$C_nH_{2n+1}O(A)_xR \qquad (I)$$

wherein
R is a $C_{1-3}$ alkyl,
A is an ethyleneoxy,
n is an integer of from 4 to 8, and
x is a number of from 3 to 25, and
whereby the wetting rate of the alkaline formulation is increased.

2. The method according to claim 1, wherein R is methyl.
3. The method according to claim 1, wherein R is ethyl.
4. The method according to claim 1, wherein R is propyl.
5. The method according to claim 1, wherein x is a number of from 5 to 15.
6. The method according to claim 1, wherein x is a number of from 5 to 12.
7. The method according to claim 1, wherein the at least one alkanol-free alkoxylate of the general formula (I) is present in the alkaline formulation in an amount of from 0.05 wt. % to 5 wt. %.
8. The method according to claim 1, wherein the at least one alkanol-free alkoxylate of the general formula (I) is present in the alkaline formulation in an amount of from 0.1 wt. % to 2 wt. %.
9. The method according to claim 1, wherein the at least one alkanol-free alkoxylate of the general formula (I) is present in the alkaline formulation in an amount of from 0.05 wt. % to 0.5 wt. %.
10. The method according to claim 1, wherein the at least one alkanol-free alkoxylate of the general formula (I) is present in the alkaline formulation in an amount of from 0.05 wt. % to 0.1 wt. %.
11. The method according to claim 1, wherein the alkaline formulation comprises water and at least one surfactant.
12. The method according to claim 1, wherein the alkaline formulation comprises water and at least one nonionic surfactant.
13. The method according to claim 1, wherein the alkaline formulation comprises at least one surfactant that exhibits a surface tension of less than 45 mN/m at 20° C. when present in an amount of 5 g/L of water.
14. The method according to claim 1, wherein the at least one alkanol-free alkoxylate of the general formula (I) increases the wetting rate of the alkaline formulation by accelerating the establishment of a reduced surface tension in the alkaline formulation.
15. The method according to claim 1, wherein the at least one alkanol-free alkoxylate of the general formula (I) increases the wetting rate of the alkaline formulation by accelerating the establishment of a reduced surface tension in the alkaline formulation in a period of less than 1 second.
16. The method according to claim 11, wherein the at least one alkanol-free alkoxylate of the general formula (I) increases the wetting rate of the alkaline formulation by accelerating the establishment of a reduced surface tension in the alkaline formulation.
17. The method according to claim 1, wherein the alkaline formulation exhibits alkali stability.
18. The method according to claim 1, wherein the alkaline formulation has a pH of more than 10.
19. The method according to claim 1, wherein the alkaline formulation has a pH of more than 12.
20. The method according to claim 1, wherein the alkaline formulation is selected from a wetting composition, a coating composition, a cleaning composition, a degreasing composition, a metal treatment composition and a metalworking composition.

* * * * *